United States Patent
Pozzoli et al.

(10) Patent No.: US 8,158,795 B2
(45) Date of Patent: Apr. 17, 2012

(54) PROCESS FOR THE PURIFICATION OF NEUROMUSCULAR BLOCKING AGENTS

(75) Inventors: Claudio Gianluca Pozzoli, Monza (IT); Franco Malanga, San Guiliano Milanese (IT); Vincenzo Redaelli, Mariano Comense (IT)

(73) Assignee: Farmabios S.p.A., Gropello Cairoli (PV) (IT)

( * ) Notice: Subject to any disclaimer, the term of this patent is extended or adjusted under 35 U.S.C. 154(b) by 432 days.

(21) Appl. No.: 12/500,926

(22) Filed: Jul. 10, 2009

(65) Prior Publication Data

US 2010/0016596 A1    Jan. 21, 2010

(30) Foreign Application Priority Data

Jul. 16, 2008 (IT) .............................. MI2008A1294

(51) Int. Cl.
*C07D 217/00* (2006.01)
*C07D 401/12* (2006.01)

(52) U.S. Cl. ........................ 546/140; 546/139
(58) Field of Classification Search ........................ None
See application file for complete search history.

(56) References Cited

FOREIGN PATENT DOCUMENTS

WO  92/00965 A   1/1992
WO  WO 03/074526 A2 *  9/2003

OTHER PUBLICATIONS

Stenlake, et al., Biodegradable Neuromuscular Blocking Agents, Eur. J. Med. Chem.—Chim. Ther., 1984, vol. 5, pp. 441-450.
Salado, et al., USP Monographs: Atracurium Besylate, European Pharmacopeia 5.2, pp. 3170-3172., 2005.
Diederen, Palladium Mediated Synthesis of N-heterocycles by Iminoannulation of Allenes, 2001, p. 137.

* cited by examiner

*Primary Examiner* — Zinna Northington Davis
(74) *Attorney, Agent, or Firm* — Lucas & Mercanti, LLP

(57) ABSTRACT

A process for the preparation of neuromuscular blocking agents with isoquinoline structure, such as atracurium besylate, doxacurium chloride, mivacurium chloride and gantacurium chloride, by chromatographic purification of their mixtures of isomers using a silica modified by treatment with a tertiary amine of formula $NR_1R_2R_3$ or a corresponding quaternary ammonium compound $N^+R_1R_2R_3R_4X^-$ wherein $R_1$, $R_2$, $R_3$ and $R_4$, the same or different, are linear or branched $C_1$-$C_4$ alkyl groups or —$CH_2$—Ar groups or two among $R_1$, $R_2$, $R_3$ and $R_4$ form a 5- or 6-membered cycle, optionally substituted with a —$CH_2$—Ar group or condensed with an Ar group, Ar being an aryl optionally substituted with one or more electrodonating groups, and $X^-$ being a suitable anion, is described.

6 Claims, No Drawings

PROCESS FOR THE PURIFICATION OF NEUROMUSCULAR BLOCKING AGENTS

FIELD OF THE INVENTION

The present invention relates to a process for the purification of neuromuscular blocking agents and, more particularly, it relates to a chromatographic process for the purification of cis-atracurium besylate and derivatives with similar isoquinoline structure by using modified silica.

BACKGROUND OF THE INVENTION

Neuromuscular blocking agents are a class of compounds for pharmacological use showing remarkable structural analogies because most of them are tetrahydropapaverine derivatives. Among the neuromuscular agents belonging to this class, atracurium besylate, doxacurium chloride, mivacurium chloride and gantacurium chloride, all isoquinoline derivatives, may be cited.

These compounds are prepared by synthetic route as mixtures of different geometrical and optical isomers which are particularly complicated to separate.

For example, atracurium besylate is a mixture of ten geometrical and optical isomers (Eur. J. Med. Chem.—Chim Ther., 1984-19, no. 5, pages 441-450).

Cis-atracurium besylate is one of these isomers, in particular the 1R-cis,1'R-cis isomer of formula

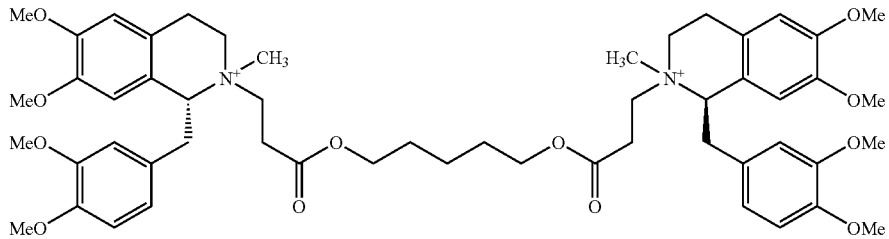

marketed as neuromuscular blocking agent under the tradename Nimbex®.

In WO92/00965 the preparation of cis-atracurium besylate by chromatography of (1R,1'R)-atracurium besylate, that is the mixture of the isomers cis-cis, cis-trans and trans-trans, is described.

The described chromatographic method is the high pressure liquid chromatography (HPLC) using silica or alumina as stationary phase and a suitable mixture of solvents as mobile phase. The preferred mixture of solvent is a mixture of methylene chloride, methanol, benzensulfonic acid in the ratio 4000:500:0.25.

However, by repeating the chromatographic purification method described in WO92/00965, the atracurium besylate isomer 1R-cis,1R'-cis cannot be obtained. On the contrary, degradation products of atracurium besylate are obtained, in particular the compounds likely obtained by Hoffman degradation, known as impurities C and F of atracurium besylate (European Pharmacopeia 5.2, pages 3170-3172).

SUMMARY OF THE INVENTION

We have now found that the degradation can be avoided by using a modified silica, so allowing to obtain the desired isomer in substantially pure form by chromatographic separation.

DETAILED DESCRIPTION OF EMBODIMENTS OF THE INVENTION

Therefore, object of the present invention is a process for the preparation of neuromuscular blocking agents with isoquinoline structure by chromatographic purification of their isomeric mixtures characterized by the use of silica modified by treatment with a tertiary amine of formula $NR_1R_2R_3$ or with its corresponding quaternary ammonium compound $N^+R_1R_2R_3R_4X^-$ wherein $R_1$, $R_2$, $R_3$ and $R_4$, the same or different, are linear or branched $C_1$-$C_4$ alkyl groups or —$CH_2$—Ar groups or two among $R_1$, $R_2$, $R_3$ and $R_4$ form a 5- or 6-membered cycle, optionally substituted with a —$CH_2$—Ar group or condensed with an Ar group, Ar being an aryl optionally substituted with one or more electrodonating groups, and $X^-$ being a suitable anion.

The neuromuscular blocking agents which can be prepared with the purification process object of the present invention are atracurium besylate, doxacurium chloride, mivacurium chloride and gantacurium chloride.

The present invention is preferably applied for the purification of atracurium besylate to obtain substantially pure 1R-cis,1'R-cis atracurium besylate by chromatographic separation, in particular with a purity higher than 98% without degradation of the product during the chromatographic process.

The modified silica used in the process of the present invention is obtained by treating commercially available silica gel with a tertiary amine of formula $NR_1R_2R_3$ or with a corresponding quaternary ammonium compound $N^+R_1R_2R_3R_4X^-$ wherein $R_1$, $R_2$, $R_3$, $R_4$ and $X^-$ have the already reported meanings.

The treatment consists in suspending the silica in a solution of the quaternary ammonium compound in a suitable solvent or mixture of solvents for some hours at room temperature. At the end of the treatment the resultant modified silica is dried for some hours under vacuum at a temperature of 50-80° C.

Alternatively, the modified silica can be prepared by covalently binding a tertiary amine of formula $NR_1R_2R_3$ to the surface of the silica by using a spacer molecule, according to conventional techniques.

The silica modified by treatment with an amine of formula $NR_1R_2R_3$ wherein at least one among $R_1$, $R_2$ and $R_3$ is a —$CH_2$—Ar group is particularly preferred and represents an object of the present invention.

A further object of the present invention is the use of modified silica obtained by treating silica gel with a tertiary amine of formula $NR_1R_2R_3$ or with a corresponding quaternary ammonium compound $N^+R_1R_2R_3R_4X^-$ wherein $R_1$, $R_2$, $R_3$, $R_4$ and $X^-$ have the already reported meanings, for the chromatographic purification of isomers of neuromuscular blocking agents with isoquinoline structure.

In the present context, linear or branched $C_1$-$C_4$ alkyl group means alkyl groups selected from methyl, ethyl, propyl, isopropyl, n.butyl, isobutyl, s.butyl and t.butyl.

A 5- or 6-membered cycle, optionally substituted by a —CH$_2$—Ar group or condensed with an Ar group means pyrrolidine, piperidine, tetraisoquinoline, indoline and similar.

Specific meanings for the Ar group are phenyl and naphthyl optionally substituted with one or more electrodonating groups, preferably C$_1$-C$_4$ alkoxy groups.

Particularly preferred Ar groups are phenyl groups optionally substituted by from one to three methoxy groups.

Specific examples of tertiary amines of formula NR$_1$R$_2$R$_3$ are trimethylamine, triethylamine, tributylamine, benzyldimethylamine, N-methyl-tetrahydropapaverine, laudanosine, 1,2,3,4-tetrahydro-6,7,8-trimethoxy-1-[(3,4,5-trimethoxyphenyl)methyl]-2-methylisoquinoline and 1,2,3,4-tetrahydro-6,7-dimethoxy-1-[(3,4,5-trimethoxy-phenyl)methyl]-2-methylisoquinoline. Specific examples of quaternary ammonium compounds N$^+$R$_1$R$_2$R$_3$R$_4$ are tetramethylammonium, benzyltrimethylammonium, N-methyl-laudanosine, N-methyl-1,2,3,4-tetrahydro-6,7,8-trimethoxy-1-[(3,4,5-trimethoxyphenyl)methyl]-2-methylisoquinoline and N-methyl-1,2,3,4-tetrahydro-6,7-dimethoxy-1-[(3,4,5-trimethoxyphenyl)methyl]-2-methylisoquinoline with X$^-$ preferably being halide, still more preferably chloride or bromide. The modified silica used in the process object of the present invention is preferably prepared by treating silica with a solution of the quaternary ammonium compound of formula N$^+$R$_1$R$_2$R$_3$R$_4$X$^-$.

Quaternary ammonium compounds particularly preferred for the preparation of the modified silica used in the process object of the present invention are tetrabutylammonium chloride and benzyltrimethylammonium chloride.

The treatment with a quaternary ammonium compound to prepare the modified silica can be carried out in any solvent or mixture of solvents in which the quaternary ammonium compound is soluble.

In a particularly preferred practical embodiment, the process object of the present invention is used for the purification of cis-atracurium besylate.

The chromatographic purification for the preparation of 1R-cis,1R'-cis atracurium besylate according to the process object of the present invention is carried out by using, as stationary phase, silica modified by treatment with a tertiary amine NR$_1$R$_2$R$_3$ or with a corresponding quaternary ammonium compound N$^+$R$_1$R$_2$R$_3$R$_4$X$^-$ wherein R$_1$, R$_2$, R$_3$ and R$_4$ have the already reported meanings, and, as mobile phase, a suitable mixture of solvents.

For practical reasons, a solvent or a mixture of solvents which will be used for the subsequent chromatographic purification of cis-atracurium besylate are preferably used.

Suitable mixtures of solvents are mixtures of a chlorinated hydrocarbon or acetonitrile with a lower aliphatic alcohol and a strong acid.

A particularly preferred chlorinated hydrocarbon is methylene chloride.

Specific examples of lower aliphatic alcohols are methanol, ethanol and propanol, methanol being particularly preferred.

Specific examples of strong acids are benzensulfonic acid, methansulfonic acid, p.toluenesulfonic acid and phosphonic acid, benzensulfonic acid being particularly preferred. The purification process object of the present invention is preferably carried out by eluting with a mixture of methylene chloride:methanol:benzensulfonic acid.

The ratio between methylene chloride and methanol in the mobile phase generally ranges from 90:10 to 70:30 with the addition of a small amount (0.005-0.5%) of benzensulfonic acid. Depending from the elution order of the isomers of atracurium besylate, it can be particularly advantageous to work under gradient.

Preferably the chromatographic purification of cis atracurium besylate is carried out with silica modified with benzyltrimethylammonium chloride. By first eluting with a mixture methylene chloride:methanol:benzensulfonic acid=90:10:0.0055, the first fractions containing the eventual heads and then the desired isomer 1R-cis,1R'-cis are separated. By working under gradient the elution is continued with a mixture methylene chloride:methanol:benzensulfonic acid=70:30:0.0055, then separating the other isomers and the eventual tails. At the end the column is washed with methylene chloride:methanol:benzensulfonic acid=50:50:0.0055% and then used again in the subsequent purification cycle without further treatments.

In order to better illustrate the present invention without limiting it, the following examples are now given.

Example 1

Preparation of Modified Silica by Adsorption of Benzyltrimethylammonium Chloride Silica (15-35 μm, 100 Å, 40 g), benzyltrimethylammonium chloride (20 g), methanol (160 ml) and benzensulfonic acid (0.0055%) were kept under stirring for 12 hours at room temperature.

The suspension was filtered and the silica dried for 16 hours under vacuum at 70° C.

Example 2

Purification of 1R-cis,1R'-cis atracurium besylate

Modified silica, prepared as described in example 1, was charged on a preparative column (45×150). After conditioning with methylene chloride:methanol:benzensulfonic acid=90:10:0.0055% (2000 ml), (R)-atracurium besylate (1 g) was charged as mixture of three isomers with 56% of isomer cis-cis. After elution with methylene chloride:methanol:benzensulfonic acid=90:10:0.0055% at 1.0 atm pressure with a flow of 8.5 ml/min, the enriched fractions containing cis-atracurium with purity ≧98% were collected. After work up as described in WO92/00965 and drying under vacuum at 40° C. up to a solid, 1R-cis,1R'-cis atracurium besylate with purity ≧98% (0.45-0.5 g—recovery about 80-90% of theoretical) was obtained.

At the end the column was washed with methylene chloride:methanol:benzensulfonic acid=50:50:0.0055%.

What is claimed is:

1. A process for the preparation of neuromuscular blocking agents with isoquinoline structure by chromatographic purification of their isomeric mixtures characterized by the use of silica modified by treatment with a tertiary amine of formula NR$_1$R$_2$R$_3$ or with its corresponding quaternary ammonium compound N$^+$R$_1$R$_2$R$_3$R$_4$X$^-$ wherein R$_1$, R$_2$, R$_3$ and R$_4$, the same or different, are linear or branched C$_1$-C$_4$ alkyl groups or —CH$_2$—Ar groups or two among R$_1$, R$_2$, R$_3$ and R$_4$ form a 5- or 6-membered cycle, optionally substituted with a —CH$_2$—Ar group or condensed with an Ar group, Ar being an aryl optionally substituted with one or more electrodonating groups, and X$^-$ being a suitable anion.

2. A process according to claim 1 for the purification of atracurium besylate, doxacurium chloride, mivacurium chloride and gantacurium chloride.

3. A process according to claim 1 for the purification of atracurium besylate.

4. A process according to claim 1, wherein the tertiary amine of formula $NR_1R_2R_3$ is selected among trimethylamine, triethylamine, tributylamine, benzyldimethylamine, N-methyl-tetrahydropapaverine, laudanosine, 1,2,3,4-tetrahydro-6,7,8-trimethoxy-1-[(3,4,5-trimethoxyphenyl)methyl]-2-methylisoquinoline and 1,2,3,4-tetrahydro-6,7-dimethoxy-1-[(3,4,5-trimethoxyphenyl)methyl]-2-methylisoquinoline.

5. A process according to claim 1, wherein the quaternary ammonium compound $N^+ R_1R_2R_3R_4$ is selected among tetramethylammonium, benzyltrimethylammonium, N-methyl-laudanosine, N-methyl-1,2,3,4-tetrahydro-6,7,8-trimethoxy-1-[(3,4,5-trimethoxyphenyl)methyl]-2-methylisoquinoline and N-methyl-1,2,3,4-tetrahydro-6,7-dimethoxy-1-[(3,4,5-trimethoxyphenyl)methyl]-2-methylisoquinoline, each as chloride or bromide.

6. A process according to claim 1 for the preparation of 1R-cis,1R'-cis atracurium besylate comprising the use of silica modified by treatment with benzyltrimethylammonium chloride.

* * * * *